(12) United States Patent
Park et al.

(10) Patent No.: US 10,448,662 B2
(45) Date of Patent: Oct. 22, 2019

(54) COMPOSITION FOR PREVENTING OR TREATING FATTY LIVER OR INSULIN RESISTANCE SYNDROME INCLUDING EXTRACELLULAR DOMAIN OF DELTA-LIKE 1 HOMOLOG

(71) Applicants: Y-Biologics Inc., Daejeon (KR); Industry-Academic Cooperation Foundation, Yonsei University, Seoul (KR)

(72) Inventors: Young Woo Park, Daejeon (KR); Bum-chan Park, Daejeon (KR); Bong-soo Cha, Seoul (KR); Yong Ho Lee, Seoul (KR); Jung Chae Lim, Daejeon (KR); Young-gyu Cho, Daejeon (KR); Joong Kyu Kim, Daejeon (KR); Jae Eun Park, Daejeon (KR); Seok Ho Yoo, Daejeon (KR)

(73) Assignees: Y-Biologics Inc., Daejeon (KR); Industry-Academic Cooperation Foundation, Yonsei University, Seoul (KR)

( * ) Notice: Subject to any disclaimer, the term of this patent is extended or adjusted under 35 U.S.C. 154(b) by 97 days.

(21) Appl. No.: 15/337,208

(22) Filed: Oct. 28, 2016

(65) Prior Publication Data
US 2017/0121380 A1    May 4, 2017

(30) Foreign Application Priority Data
Oct. 29, 2015    (KR) .................. 10-2015-0150871

(51) Int. Cl.
| | |
|---|---|
| A61K 38/17 | (2006.01) |
| A61K 38/18 | (2006.01) |
| C07K 14/47 | (2006.01) |
| C07K 14/475 | (2006.01) |
| C07K 19/00 | (2006.01) |
| A23L 33/17 | (2016.01) |
| A61K 47/68 | (2017.01) |

(52) U.S. Cl.
CPC .......... *A23L 33/17* (2016.08); *A61K 38/1709* (2013.01); *A61K 38/18* (2013.01); *A61K 47/68* (2017.08); *C07K 14/4713* (2013.01); *C07K 19/00* (2013.01); *C07K 14/475* (2013.01); *C07K 2319/30* (2013.01)

(58) Field of Classification Search
CPC .... A61K 38/1709; A61K 38/18; A61K 38/19; C07K 2319/00; C07K 14/00; C07K 14/47; C07K 2319/30; C07K 14/475; C07K 14/52
See application file for complete search history.

(56) References Cited

U.S. PATENT DOCUMENTS

| | | | |
|---|---|---|---|
| 6,660,843 B1 * | 12/2003 | Feige .................. | C07K 14/505 530/350 |
| 8,785,382 B2 * | 7/2014 | Kilpatrick ........... | A61K 9/0019 514/7.4 |
| 9,388,223 B2 * | 7/2016 | Lee ........................ | A61K 38/16 |

FOREIGN PATENT DOCUMENTS

KR    10-2012-0113174 A    10/2012

OTHER PUBLICATIONS

ACE Position Statement, Endocr Pract 9(3): 240-252, 2003.*
Bork, A. Powers and pitfalls in sequence analysis: the 70% hurdle. Genome Res 10: 398-400, 2000.*
Bork et al. Go hunting in sequence databases but watch out for the traps. Trends in Genetics. 12(10): 425-427, 1996.*
Brenner, S.E. Errors in genome function. Trends in Genetics 15(4): 132-133, 1999.*
Doerks et al. Protein annotation: detective work for function prediction. Trends in Genetics 14(6): 248-250, 1998.*
Ighbariya et al. Insulin resistance, prediabetes, metabolic syndrome: what should every pediatrician know? J Clin Res Pediatr Endocrinol 9(Suppl 2): 49-57, 2017.*
Lee et al. Exogenous administration of DLK1 ameliorates hepatic steatosis and regulates gluconeogenesis via activation of AMPK. Int J Obesity 40: 356-365, published online Sep. 22, 2015.*
Mei et al. Only the large soluble form of preadipocyte factor-1 (Pref-1), but not the small soluble and membrane forms, inhibits adipocyte differentiation: role of alternative splicing. Biochem J 364: 137-144, 2002.*
Ngo et al. Computational complexity, protein structure prediction, and the Levinthal paradox. The Protein Folding Problem and Tertiary Structure Prediction, pp. 492-495, 1994.*
Reaven, G.M. The insulin resistance syndrome: definition and dietary approaches to treatment. Annu Rev Nutr 25: 391-406, 2005.*
Skolnick et al. From genes to protein structure and function: novel applications of computational approaches in the genomic era. Trends in Biotech 18(1): 34-39, 2000.*
Suras et al. Cleavage of membrane-associated pref-1 generates a soluble inhibitor of adipcoyte differentiation. Mol Cell Biol 17(2): 977-988, 1997.*
Smith et al. The challenges of genome sequence annotation or "The devil is in the details". Nature Biotech 15: 1222-1223, 1997.*
Tokuriki et al. Stability effects of mutations and protein evolvability. Curr Opin Structural Biol 19: 596-604, 2009.*
Wells. J.A. Additivity of mutational effects in proteins. Biochemistry 29 (37): 8509-8517, 1990.*

(Continued)

*Primary Examiner* — Bridget E Bunner
(74) *Attorney, Agent, or Firm* — Licata & Tyrrell P.C.

(57) ABSTRACT

The present invention relates to compositions and methods for treating fatty liver, steatohepatitis, or liver cirrhosis as well as insulin resistance and aging by administration of a DLK1-Fc fusion protein constructed by conjugation of an extracellular domain of DLK1 or a fragment thereof with a human antibody Fc region. Also provided are health functional foods containing a DLK1-Fc fusion protein constructed by conjugation of an extracellular domain of DLK1 (delta-like 1 homolog) or a fragment thereof with a human antibody Fc region as an active ingredient.

1 Claim, 7 Drawing Sheets

Specification includes a Sequence Listing.

(56) References Cited

OTHER PUBLICATIONS

Yun et al. Effects of exogenous DLK1-Fc treatment on insulin secretion and insulin sensitivity in an animal model of diet-induced obsesity. Diabetologia 56(Suppl 1): S268-269, 2013.*
UniProt Accession No. P80370; May 18, 2010 (9 total pages).*
Bujak et al. A monoclonal antibody to human DLK1 reveals differential expression in cancer and absence in healthy tissue. Antibodies 4: 71-87, Apr. 2015.*
Charalambous et al. DLK1/PREF1 regulates nutrient metabolism and protects from steatosis. Proc Natl Acad Sci USA 111(45): 16088-16093, 2014.*
Carlsson et al. "Growth Hormone and Prolactin Stimulate the Expression of Rat Preadipocyte Factor-1/D-Like Protein in Pancreatic Islets: Molecular Cloning and Expression Pattern during Development and Growth of the Endocrine Pancreas" Endocrinology 1997 138:3940-8.
Halder et al. "Cloning of a Membrane-Spanning Protein with Epidermal Growth Factor-Like Repeat Motifs from Adrenal Glomerulosa Cells" Endocrinology 1998 139:3316-28.
Jensen et al. "Protein structure of fetal antigen 1 (FA1) A novel circulating human epidermal-growth-factor-like protein expressed in neuroendocrine tumors and its relation to the gene products of dlk and pG2" European Journal of Biochemistry 1994 225:83-92.
Kaneta et al. "A Role for Pref-1 and HES-1 in Thymocyte Development" Journal of Immunology 2000 164: 256-64.
Pajvani et al."Inhibition of Notch signaling ameliorates insulin resistance in a FoxO1-dependent manner" Nat Med 2011 17:961-967.
Schulman G.I. "Cellular mechanisms of insulin resistance" J. Clin. Invest. 2000 106:171-176.
Smas C.M. & Sul H.S. "Pref-1, a protein containing EGF-like repeats, inhibits adipocyte differentiation" Cell 1993 73:725-734.
Wang Y. & Sul H.S. "Ectodomain shedding of preadipocyte factor 1 (Pref-1) by tumor necrosis factor alpha converting enzyme (TACE) and inhibition of adipocyte differentiation" Molecular and cellular biology 2006 26(14): 5421-5435.
2014 International Conference on Diabetes & Metabolism Poster OP9-3 Oct. 16-18, 2014.

* cited by examiner

COMPOSITION FOR PREVENTING OR TREATING FATTY LIVER OR INSULIN RESISTANCE SYNDROME INCLUDING EXTRACELLULAR DOMAIN OF DELTA-LIKE 1 HOMOLOG

INTRODUCTION

This patent application claims the benefit of priority from KR Patent Application No. 10-2015-0150871 filed Oct. 29, 2015, the contents of which is herein incorporated by reference in its entirety.

This research was supported by a grant of the Korea Health Industry Development Institute (KHIDI), funded by the Ministry of Health & Welfare, Republic of Korea (grant number: HI14C1135).

BACKGROUND OF THE INVENTION

The present invention relates to a composition for preventing or treating fatty liver or insulin resistance syndrome comprising an extracellular domain of DLK1 (delta-like 1 homolog) as an active ingredient.

Fatty liver is the condition of abnormal fat accumulation in hepatocytes, and is medically the disease state caused when the content of triglyceride exceeds at least 5% of the total liver weight. In general, fatty liver is divided into two categories; alcoholic fatty liver (alcoholic fatty liver disease, ALD) caused by continual excessive drinking and non-alcoholic fatty liver (non-alcoholic fatty liver disease, NALFD) displaying similar liver tissue features to alcoholic fatty liver even though there is no alcohol drinking. According to high fat and high calorie diet in the modern society, which increases adult diseases, non-alcoholic fatty liver disease (NALFD) is noticed in 20~30% of adult population in advanced countries, among which 2~3% of the people progress to nonalcoholic steatohepatitis (NASH) with displaying steatohepatitis features accompanied with tissue fibrosis and inflammation that increases the risk of liver cirrhosis, liver failure, and liver cancer.

Insulin plays an important role in using blood glucose as an energy source. Insulin delivers glucose to each cell by using an insulin receptor on each cell membrane. Insulin resistance is a glucose/nutrition associated metabolism disorder, which is caused when the liver tissue, adipose tissue, and muscle tissue do not respond normally to a normal concentration of insulin. Insulin promotes glucose absorption in muscle or regulates blood sugar by suppressing glucose production in the liver. Insulin resistance indicates such state that the insulin activity is reduced under the normal insulin concentration (Schulman G I, J. Clin. Invest. 106:171-176(2000)). Insulin resistance has been known as a major cause of many dangerous factors causing such diseases as type II diabetes, obesity, hypertension, hypertriglyceridemia, low HDL cholesterolemia, coronary artery disease, and artherosclerosis.

Noch signal transduction has been well preserved in from vertebrates to invertebrates in the prospect of evolution, which allegedly plays an important role in determining the cell fate in the early developmental stage. Notch signal transduction is also known as a key factor in the regulation of differentiation of nerve, eyeballs, lymph, muscle, and blood corpuscles. Abnormal regulation of Notch signal transduction is directly involved in the development of various diseases including congenital diseases and cancer. Notch signal transduction has also been confirmed to be an important factor involved in non-alcoholic fatty liver disease and diabetes. Notch activation promotes glucose synthesis and fat generation in hepatocytes, and thereby increases insulin resistance (Pajvani U B et al., Nat Med 2011; 17: 961-967).

Mammals have 4 Notch receptors (Notch 1, 2, 3, and 4). Each Notch receptor is synthesized as a 300~350 kDa protein and forms a heterodimer on the cell surface when S1 region is cut off by furin-like convertase in the Golgi body. 4 Notch ligands (Jagged-1/2 and Delta-like-1/3/4) were also identified in mammals.

DLK1 (delta-like protein 1) belonging to notch/delta/serrate family is a transmembrane glycoprotein encoded by dlk1 gene on chromosome 14q32, which is composed of 383 amino acids. This protein is composed of 280 extracellular domains, 24 transmembrane domains, and 56 intracellular domains. It has 6 epidermal growth factor like repeat domains outside of the cell membrane and 3 N-glycosylation sites and 7 O-glycosylation sites. DLK1 is a transmembrane protein and at the same time acts as an independent protein functioning by shedding when outer layer of the cell membrane is fallen apart from the cell membrane by tumor necrosis factor alpha converting enzyme (TACE) (Yuhui Wang and Hei Sook Sul, Molecular and cellular biology. 26(14): 5421-5435, 2006).

DLK1 (delta-like 1 homolog) is mainly expressed in the early developmental stage of embryonic tissue (Smas C M et al., Cell. 73: 725-34, 1993; Kaneta M et al., Journal of Immunology. 164: 256-64, 2000) and placenta. It is especially detected at a high level in maternal serum, because of which it has been known as fetal antigen 1 (FA1) (Jensen C H et al., European Journal of Biochemistry. 225: 83-92, 1994). According to the previous reports, DLK1 is also expressed in glandular cells, ovary, and skeletal myotubes, etc. DLK1 expression disappears in most tissues after birth and is only observed in such specific cells as preadipocytes, pancreatic islet cells (Carlsson C et al., Endocrinology. 138:3940-8, 1997), thymic stromal cells (Kaneta M et al., Journal of Immunology. 164: 256-64, 2000), and adrenal gland cells (Halder S K et al., Endocrinology. 139: 3316-28, 1998).

Numbers of research results support that DLK1 interacts with Notch and has the activity of inhibiting Notch signal transduction. The water-soluble extracellular domain of DLK1 produces TACE (tumor necrosis factor-α converting enzyme) protease, by which it can inhibit adipogenesis in vivo and in vitro (Wang Y et al., Mol Cell Biol 2006; 26: 5421-5435). Based on those research results, it is expected that DLK1 can be developed as a target material to regulate metabolic disorders observed in fatty liver, insulin resistance syndrome, type II diabetes, and non-alcoholic liver disease.

The present inventors tried to develop a novel agent to treat and improve fatty liver or insulin resistance syndrome. In the course of the study, the present inventors confirmed that a pharmaceutical composition comprising the DLK1-Fc fusion protein constructed by the conjugation of an extracellular domain of DLK1 or a fragment thereof with a human antibody Fc region could reduce triglyceride in the liver, improve glucose and insulin resistance, and inhibit fat accumulation and glucose synthesis in the liver, leading to the completion of the present invention.

SUMMARY OF THE INVENTION

It is an object of the present invention to provide a composition for preventing or treating fatty liver or insulin resistance syndrome comprising an extracellular domain of DLK1 (delta-like 1 homolog) as an active ingredient To achieve the above object, the present invention provides a pharmaceutical composition comprising the DLK1-Fc fusion protein constructed by the conjugation of an extracellular domain of DLK1 or a fragment thereof with a human antibody Fc region as an active ingredient for the prevention and treatment of fatty liver, steatohepatitis, or liver cirrhosis.

The present invention also provides a health functional food comprising the DLK1-Fc fusion protein constructed by the conjugation of an extracellular domain of DLK1 or a fragment thereof with a human antibody Fc region as an active ingredient for the prevention or improvement of fatty liver, steatohepatitis, or liver cirrhosis.

The present invention also provides a pharmaceutical composition comprising the DLK1-Fc fusion protein constructed by the conjugation of an extracellular domain of DLK1 or a fragment thereof with a human antibody Fc region as an active ingredient for the prevention and treatment of insulin resistance syndrome.

The present invention also provides a health functional food comprising the DLK1-Fc fusion protein constructed by the conjugation of an extracellular domain of DLK1 or a fragment thereof with a human antibody Fc region as an active ingredient for the prevention or improvement of insulin resistance syndrome.

The present invention also provides a pharmaceutical composition comprising the DLK1-Fc fusion protein constructed by the conjugation of an extracellular domain of DLK1 or a fragment thereof with a human antibody Fc region as an active ingredient for the prevention and treatment of aging.

The present invention also provides a health functional food comprising the DLK1-Fc fusion protein constructed by the conjugation of an extracellular domain of DLK1 or a fragment thereof with a human antibody Fc region as an active ingredient for the prevention or improvement of aging.

The present invention relates to a composition comprising an extracellular domain of DLK1 (delta-like 1 homolog) as an active ingredient for the prevention and treatment of fatty liver or insulin resistance syndrome. More precisely, a water-soluble DLK1-Fc fusion protein was constructed by fusing a water-soluble extracellular domain of DLK1 (delta-like 1 homolog) with a human antibody Fc, and this construct was inserted in a mouse. As a result, it was observed that triglyceride (TG) and lipid droplets were significantly reduced in the mouse, and fasting blood glucose and random blood glucose were also significantly reduced, suggesting that glucose and insulin resistance was improved. And the therapeutic effect of the DLK1-Fc fusion protein on pancreatic islet and adipose tissue inflammation was confirmed in vivo and in vitro. The inhibitory effect of the DLK1-Fc fusion protein on fat accumulation and liver glucose production through AMPK activation was also confirmed. Therefore, a pharmaceutical composition comprising the DLK1-Fc fusion protein constructed by the conjugation of an extracellular domain of DLK1 or a fragment thereof with a human antibody Fc region of the present invention as an active ingredient can be effectively used for the prevention and treatment of fatty liver or insulin resistance syndrome (metabolic syndrome).

BRIEF DESCRIPTION OF THE DRAWINGS

The application of the preferred embodiments of the present invention is best understood with reference to the accompanying drawings, wherein:

FIG. 1, view a: a diagram illustrating the structures of DLK1 and DLK1-domain Fc region.

FIG. 1, view b: a diagram illustrating the db/db mouse liver tissue.

FIG. 1, view c: a diagram illustrating the level of triglyceride (TG) in db/db mouse.

FIG. 1, view d: a diagram illustrating the weight of the liver of db/db mouse.

FIG. 1, view e: a diagram illustrating the glycogen content in the liver of the db/db mouse.

FIG. 1, view f: a diagram illustrating the blood AST and ALT levels in db/db mouse.

FIG. 2, view c: a diagram illustrating the result of oral glucose tolerance test in db/db mouse.

FIG. 2, view d: a diagram illustrating the result of insulin tolerance test in db/db mouse.

FIG. 2, view e: a diagram illustrating the levels of cholesterol, triglyceride, and NEFA in db/db mouse.

FIG. 3, view a: a diagram illustrating the insulin positive region in the db/db mouse pancreas, stained by immunohistochemistry.

FIG. 3, view b: a diagram illustrating the β-cell fraction in the db/db mouse pancreas.

FIG. 3, view c: a diagram illustrating the β-cell mass in the db/db mouse pancreas.

FIG. 3, view d: a diagram illustrating the result of immunohistochemistry using anti-F4/80 antibody in the db/db mouse epididymis fat body.

FIG. 3, view e: a diagram illustrating the percentage of F4/80 positive cells in the db/db mouse epididymis fat body.

FIG. 3, view f: a diagram illustrating the expression of IL-1β in the db/db mouse epididymis fat body.

FIG. 3, view g: a diagram illustrating the expression of iNOS in the db/db mouse epididymis fat body.

FIG. 4, view a: a diagram illustrating the expressions of AMPK, phosphorylated AMPK, ACC, and phosphorylated ACC in db/db mouse.

FIG. 4, view b: a diagram illustrating the mRNA expressions of CPT1, ACOX, and ACADM in the db/db mouse liver.

FIG. 4, view c: a diagram illustrating the expressions of AMPK, phosphorylated AMPK, ACC, and phosphorylated ACC in C57BL/6J mouse.

FIG. 4, view d: a diagram illustrating the expressions of AMPK, phosphorylated AMPK, ACC, and phosphorylated ACC in primary hepatocytes.

FIG. 4, view e: a diagram illustrating the expressions of AMPK, phosphorylated AMPK, ACC, and phosphorylated ACC in HepG2 cells.

FIG. 5, view a: a diagram illustrating the HepG2 cells stained with oil red O after the treatment of DLK1-Fc fusion protein and palmitate.

FIG. 5, view b: a diagram illustrating the quantitative analysis of 5a.

FIG. 5, view c: a diagram illustrating the expression of SREBP-1c in the HepG2 cell nucleus.

FIG. 6, view a: a diagram illustrating the level of fasting blood glucose in C57BL/6J mouse.

FIG. 6, view b: a diagram illustrating the level of random blood glucose in C57BL/6J mouse.

FIG. 6, view c: a diagram illustrating the mRNA expressions of G6Pase and PEPCK in the C57BL/6J mouse liver.

FIG. 6, view d: a diagram illustrating the mRNA expressions of G6Pase and PEPCK in the db/db mouse liver.

FIG. 6, view e: a diagram illustrating the glucose production by the DLK1-Fc fusion protein in HepG2 cells.

FIG. 6, view f: a diagram illustrating the mRNA expression of PEPCK in HepG2 cells FIG. 6, view g: a diagram illustrating the expressions of Akt and phosphorylated Akt in HepG2 cells, measured by immunoblotting.

FIG. 6, view h: a diagram illustrating the expression changes of FOXO1 by the DLK1-Fc fusion protein in HepG2 cells, confirmed in the nucleus and cytoplasm.

FIG. 6, view i: a diagram illustrating the result of fluorescence immunoassay using anti-FOXO1 antibody performed in HepG2 cells.

FIG. 6, view j: a diagram illustrating the quantitative analysis of FIG. 6*i*.

FIG. 6, view k: a diagram illustrating the mechanism of the DLK1-Fc fusion protein.

FIG. 7, view a: a diagram illustrating the structures of DLK1 and DLK1-domain Fc region.

FIG. 7, view b: a diagram illustrating the improvement of hepatic steatosis by the DLK1-Fc fusion protein in the db/db mouse liver tissue.

FIG. 7, view c: a diagram illustrating the level changes of triglyceride (TG) by the DLK1-Fc fusion protein in db/db mouse.

FIG. 7, view d: a diagram illustrating the decrease of fasting blood glucose by the DLK1-Fc fusion protein in db/db mouse.

FIG. 7, view e: a diagram illustrating the improvement of the phosphorylations of AMPK and ACC by the DLK1-Fc fusion protein in db/db mouse.

FIG. 7, view f: a diagram illustrating the mechanism of the DLK1-Fc fusion protein.

DETAILED DESCRIPTION OF THE INVENTION

Figure 1:
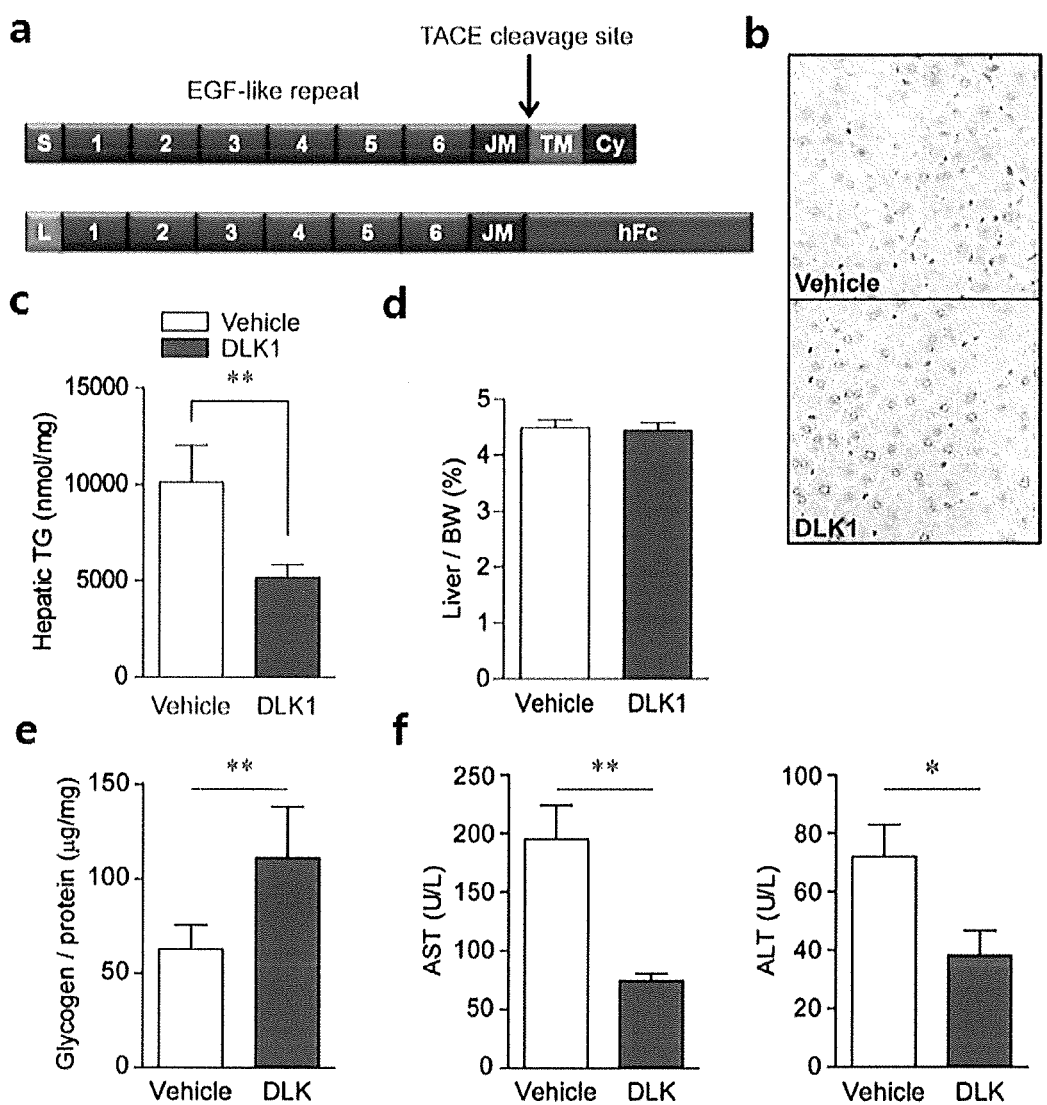
FIG. 1, inclusive of views a, b, c, d, e, and f, is a set of diagrams illustrating the improvement of hepatic steatosis by the water-soluble DLK1-Fc fusion protein in db/db mouse.

The present invention provides a pharmaceutical composition comprising the DLK1-Fc fusion protein constructed by the conjugation of an extracellular domain of DLK1 (delta-like 1 homolog) or a fragment thereof with a human antibody Fc region as an active ingredient for the prevention and treatment of fatty liver, steatohepatitis, or liver cirrhosis.

The said DLK1 is characteristically composed of the amino acid sequence represented by SEQ ID NO:1, and the extracellular water-soluble domain of the said DLK1 is characteristically composed of the amino acid sequence represented by SEQ ID NO:2. The said human antibody Fc region herein is characteristically composed of the amino acid sequence represented by SEQ ID NO:3 and the DLK1-Fc fusion protein is characteristically composed of the amino acid sequence represented by SEQ ID NO:4.

The said composition herein characteristically reduces triglyceride in the liver.

The said composition can be used as a preventive or therapeutic composition for fatty liver, steatohepatitis, or liver cirrhosis.

To prepare the DLK1-Fc fusion protein, pYK602-His-DLK1 recombinant vector was first constructed, which was inserted in 293E cells, followed by the expression and purification thereof. Particularly, to clone DLK1 in pYK602-His vector, PCR was performed using the DNA library mix (kidney, placenta, pancreas, and liver mixture) as a template with primers, resulting in the amplification of an extracellular domain of DLK1. Sfil restriction enzyme reaction was performed with the obtained PCR product. The reaction product was inserted in pYK602-His vector, resulting in the construction of the recombinant vector pYK602-His-DLK1. Then, pYK602-His-DLK1 DNA was inserted in 293E cells, followed by purification with A column. The purified DLK1-Fc protein was pH-neutralized, followed by dialysis using PPS (potassium phosphate saline) buffer. BCA assay was performed for the quantification. SDS-PAGE was performed to confirm the purification and quantification. Bacterial endotoxin was eliminated from the purified DLK1-Fc fusion protein by using EndoTrap Red column. As a result, DLK1-Fc fusion protein was constructed (Korean Patent No. 10-0982170).

In a preferred embodiment of the present invention, the inventors constructed the water-soluble DLK1-Fc fusion protein by fusing an extracellular domain of DLK1 (delta-like 1 homolog) with a human antibody Fc. Then, the constructed water-soluble DLK1-Fc fusion protein was administered to db/db mouse for 4 weeks. As a result, triglyceride (TG) and lipid droplets were significantly reduced in the db/db mouse (see FIG. 1), and fasting and random blood glucose was also significantly reduced in the mouse treated with the water-soluble DLK1-Fc fusion protein, compared with the control (see FIG. 2). Therefore, it was confirmed that the treatment of the water-soluble DLK1-Fc fusion protein improved glucose and insulin resistance in the treated mouse. In the db/db mouse group treated with the DLK1-Fc fusion protein, the infiltration of F4/80-positive macrophages was significantly lowered, indicating that the DLK1-Fc fusion protein suppressed the mRNA expressions of inflammatory cytokines such as interleukin-1β and iNOS (see FIG. 3). In the meantime, the phosphorylation of Thr$^{172}$ in AMPK-α was improved in the db/db mouse group treated with the DLK1-Fc fusion protein (see FIG. 4), and accordingly fat accumulation was suppressed according to the activation of AMPK induced by the DLK1-Fc fusion protein (see FIG. 5). The DLK1-Fc fusion protein suppressed the expressions of gluconeogenesis genes such as PEPCK and G6Pase by controlling the AMPK activation, and accordingly suppressed glucogenesis in the liver (see FIG. 6). Therefore, the pharmaceutical composition comprising the DLK1-Fc fusion protein constructed by the conjugation of an extracellular domain of DLK1 (delta-like 1 homolog) or a fragment thereof with a human antibody Fc region as an active ingredient can be effectively used for the prevention and treatment of fatty liver, steatohepatitis, or liver cirrhosis.

The composition of the present invention can contain the DLK1-Fc fusion protein constructed by the conjugation of an extracellular domain of DLK1 (delta-like 1 homolog) or a fragment thereof with a human antibody Fc region as an active ingredient at the concentration of 0.1~99.9 weight % by the total weight of the composition and can additionally contain a pharmaceutically acceptable carrier, excipient, or diluent.

The composition of the present invention can be administered orally or parenterally and be used in general forms of pharmaceutical formulation. That is, the composition of the present invention can be prepared for oral or parenteral administration by mixing with generally used diluents or excipients such as fillers, extenders, binders, wetting agents, disintegrating agents and surfactants. Solid formulations for oral administration are tablets, pills, powders, granules and capsules. These solid formulations are prepared by mixing the compound with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration excipients, suspensions, emulsions, lyophilized preparations and suppositories.

Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc.

The composition of the present invention can be administered orally or parenterally. The parenteral administration herein can be performed by topical administration or intraperitoneal injection, intrarectal injection, intravenous injection, intramuscular injection, subcutaneous injection, intrauterine injection, or intracerebroventricular injection.

The composition of the present invention is administered according to the pharmaceutically effective dose. The term "pharmaceutically effective dose" herein indicates the amount enough to treat the disease with applicable, reasonable or risky concentration. The dose can be determined by considering many factors such as the type of disease, severity of the disease, activity of the drug, sensitivity to the drug, administration frequency and pathway, excretion, term of treatment, co-treatment drug and other factors regarded as relevant in the medicinal field. The composition of the present invention can be administered separately as an independent drug or co-treated with other drugs together. It can be administered with the conventional treating agents stepwise or simultaneously. The administration can be either single treatment or multiple administrations. It is important to administer the composition in such a manner that can bring a maximum effect with a minimum dose which is safe amount for not causing side effects, and this decision can be made by those in the art with considering all the factors mentioned above.

The effective dose of the composition of the present invention can be determined according to weight, age, gender, health condition, diet, administration frequency, administration method, excretion and severity of a disease. The dose is 0.01~2000 mg/kg per day, preferably 0.01~1500 mg/kg per day, and more preferably 0.1~1000 mg/kg per day, and administration frequency is preferably 1~6 times a day.

The composition of the present invention can be administered alone or together with surgical operation, hormone therapy, chemo-therapy and biological regulators.

The present invention also provides a health functional food comprising the DLK1-Fc fusion protein constructed by the conjugation of an extracellular domain of DLK1 or a fragment thereof with a human antibody Fc region as an active ingredient for the prevention or improvement of fatty liver, steatohepatitis, or liver cirrhosis.

The said DLK1 is characteristically composed of the amino acid sequence represented by SEQ ID NO:1, and the extracellular water-soluble domain of the said DLK1 is characteristically composed of the amino acid sequence represented by SEQ ID NO:2. The said human antibody Fc region herein is characteristically composed of the amino acid sequence represented by SEQ ID NO:3 and the DLK1-Fc fusion protein is characteristically composed of the amino acid sequence represented by SEQ ID NO:4.

The said health functional food herein characteristically reduces triglyceride in the liver.

The said health functional food can be used as a composition for the prevention and improvement of fatty liver, steatohepatitis, or liver cirrhosis.

In a preferred embodiment of the present invention, the inventors constructed the water-soluble DLK1-Fc fusion protein by fusing an extracellular domain of DLK1 (delta-like 1 homolog) with a human antibody Fc. Then, the constructed water-soluble DLK1-Fc fusion protein was administered to db/db mouse for 4 weeks. As a result, triglyceride (TG) and lipid droplets were significantly reduced in the db/db mouse (see FIG. 1), and fasting and random blood glucose was also significantly reduced in the mouse treated with the water-soluble DLK1-Fc fusion protein, compared with the control (see FIG. 2). Therefore, it was confirmed that the treatment of the water-soluble DLK1-Fc fusion protein improved glucose and insulin resistance in the treated mouse. The present inventors further confirmed the therapeutic effect of the DLK1-Fc fusion protein on pancreatic islet and adipose tissue inflammation (see FIG. 3) and the effect of inhibiting fat accumulation and glucogenesis in the liver by taking advantage of AMPK activation (see FIG. 5 and FIG. 6). Therefore, the health functional food comprising the DLK1-Fc fusion protein constructed by the conjugation of an extracellular domain of DLK1 (delta-like 1 homolog) or a fragment thereof with a human antibody Fc region as an active ingredient can be effectively used for the prevention and improvement of fatty liver, steatohepatitis, or liver cirrhosis.

The health functional food of the present invention can additionally include various flavors or natural carbohydrates. The natural carbohydrates above can be one of monosaccharides such as glucose and fructose, disaccharides such as maltose and sucrose, polysaccharides such as dextrin and cyclodextrin, and glucose alcohols such as xylytole, sorbitol and erythritol. Besides, natural sweetening agents such as thaumatin and stevia extract, and synthetic sweetening agents such as saccharin and aspartame can be included as a sweetening agent. The content of the natural carbohydrate is preferably 0.01~0.04 weight part and more preferably 0.02~0.03 weight part per 100 weight part of the composition.

In addition to the ingredients mentioned above, the health functional food of the present invention can include a variety of nutrients, vitamins, minerals, flavors, coloring agents, pectic acid and its salts, alginic acid and its salts, organic acid, protective colloidal viscosifiers, pH regulators, stabilizers, antiseptics, glycerin, alcohols, carbonators which used to be added to soda, etc. All the mentioned ingredients can be added singly or together. The mixing ratio of those ingredients does not matter in fact, but in general, each can be added by 001~0.1 weight part per 100 weight part of the health functional food of the present invention.

The present invention also provides a pharmaceutical composition comprising the DLK1-Fc fusion protein constructed by the conjugation of an extracellular domain of DLK1 or a fragment thereof with a human antibody Fc region as an active ingredient for the prevention and treatment of insulin resistance syndrome.

The said DLK1 is characteristically composed of the amino acid sequence represented by SEQ ID NO:1, and the extracellular water-soluble domain of the said DLK1 is characteristically composed of the amino acid sequence represented by SEQ ID NO:2. The said human antibody Fc region herein is characteristically composed of the amino acid sequence represented by SEQ ID NO:3 and the DLK1-Fc fusion protein is characteristically composed of the amino acid sequence represented by SEQ ID NO:4.

The said composition herein characteristically reduces triglyceride in the liver.

The said composition can be used as a preventive or therapeutic composition insulin resistance syndrome.

The present invention also provides a health functional food comprising the DLK1-Fc fusion protein constructed by the conjugation of an extracellular domain of DLK1 or a fragment thereof with a human antibody Fc region as an active ingredient for the prevention or improvement of insulin resistance syndrome.

The said DLK1 is characteristically composed of the amino acid sequence represented by SEQ ID NO:1, and the extracellular water-soluble domain of the said DLK1 is characteristically composed of the amino acid sequence represented by SEQ ID NO:2. The said human antibody Fc region herein is characteristically composed of the amino acid sequence represented by SEQ ID NO:3 and the DLK1-Fc fusion protein is characteristically composed of the amino acid sequence represented by SEQ ID NO:4.

The said health functional food herein characteristically reduces triglyceride in the liver.

The said health functional food can be used as a composition for the prevention and improvement of insulin resistance syndrome.

The present invention also provides a pharmaceutical composition comprising the DLK1-Fc fusion protein constructed by the conjugation of an extracellular domain of DLK1 or a fragment thereof with a human antibody Fc region as an active ingredient for the prevention and treatment of aging.

The present invention also provides a health functional food comprising the DLK1-Fc fusion protein constructed by the conjugation of an extracellular domain of DLK1 or a fragment thereof with a human antibody Fc region as an active ingredient for the prevention or improvement of aging.

The said DLK1 is characteristically composed of the amino acid sequence represented by SEQ ID NO:1, and the extracellular water-soluble domain of the said DLK1 is characteristically composed of the amino acid sequence represented by SEQ ID NO:2. The said human antibody Fc region herein is characteristically composed of the amino acid sequence represented by SEQ ID NO:3 and the DLK1-Fc fusion protein is characteristically composed of the amino acid sequence represented by SEQ ID NO:4.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Construction of a Water-Soluble DLK1 Protein

To investigate the metabolism of DLK1 (delta-like 1 homolog) in fatty liver and diabetic animal models, the present inventors constructed a water-soluble DLK1 protein composed of an extracellular domain located at N-terminal of DLK1.

Particularly, the recombinant protein contained 6 EGF-like domains and the area resembling 25~302 residues of DLK1 (P80370, UniProt Knowledgebase), and was fused with human antibody Fc. The present inventors constructed pYK602-sDLK1 plasmid containing the secretion and CMV promoter signal sequences, and the expression was induced by the conventional method well informed to those in the art. The purification was performed by using protein A-Sepharose (GE, Sweden). The purity of the eluted protein was confirmed by Coomassie staining after SDS-PAGE, and the sequences are shown in Table 1 below.

TABLE 1

| Composition | Sequence |
| --- | --- |
| DLK1 (whole sequence) (SEQ ID NO: 1) | MTATEALLRVLLLLLAFGHSTYGAECFPACNPQNGFCED DNVCRCQPGWQGPLCDQCVTSPGCLHGLCGEPGQCICTD GWDGELCDRDVRACSSAPCANNRTCVSLDDGLYECSCAP GYSGKDCQKKDGPCVINGSPCQHGGTCVDDEGRASHASC LCPPGFSGNFCEIVANSCTPNPCENDGVCTDIGGDFRCR CPAGFIDKTCSRPVTNCASSPCQNGGTCLQHTQVSYECL CKPEFTGLTCVKKRALSPQQVTRLPSGYGLAYRLTPGVH ELPVQQPEHRILKVSMKELNKKTPLLTEGQAICFTILGV LTSLVVLGTVGIVFLNKCETWVSNLRYNHMLRKKKNLLL QYNSGEDLA VNIIFPEKIDMTTFSKEAGDEEI |
| Extracellular domain of DLK1-Fc (DLK1 domain) (SEQ ID NO: 2) | ECFPACNPQNGFCEDDNVCRCQPGWQGPLCDQCVTSPGC LHGLCGEPGQCICTDGWDGELCDRDVRACSSAPCANNRT CVSLDDGLYECSCAPGYSGKDCQKKDGPCVINGSPCQHG GTCVDDEGRASHASCLCPPGFSGNFCEIVANSCTPNPCE NDGVCTDIGGDFRCRCPAGFIDKTCSRPVTNCASSPCQN GGTCLQHTQVSYECLCKPEFTGLTCVKKRALSPQQVTRL PSGYGLAYRLTPGVHELPVQQPEHRILKVSMKELNKKTP LLTEG |
| IgG1 Fc domain (SEQ ID NO: 3) | DKTHTCPPCPAPELLGGPSVFLFPPKPKDTLMISRTPEV TCVVVDVSHEDPEVKFNWYVDGVEVHNAKTKPREEQYNS TYRVVSVLTVLHQDWLNGKEYKCKVSNKALPAPIEKTIS KAKGQPREPQVYTLPPSRDELTKNQVSLTCLVKGFYPSD IAVEWESNGQPENNYKTTPPVLDSDGSFFLYSKLTVDKS RWQQGNVFSCSVMHEALHNHYTQKSLSLSPGK |
| DLK1-Fc (SEQ ID NO: 4) | ECFPACNPQNGFCEDDNVCRCQPGWQGPLCDQCVTSPGC LHGLCGEPGQCICTDGWDGELCDRDVRACSSAPCANNRT CVSLDDGLYECSCAPGYSGKDCQKKDGPCVINGSPCQHG GTCVDDEGRASHASCLCPPGFSGNFCEIVANSCTPNPCE |

TABLE 1-continued

| Composition | Sequence |
|---|---|
| | NDGVCTDIGGDFRCRCPAGFIDKTCSRPVTNCASSPCQN GGTCLQHTQVSYECLCKPEFTGLTCVKKRALSPQQVTRL PSGYGLAYRLTPGVHELPVQQPEHRILKVSMKELNKKTP LLTEGDKTHTCPPCPAPELLGGPSVFLFPPKPKDTLMIS RTPEVTCVVVDVSHEDPEVKFNWYVDGVEVHNAKTKPRE EQYNSTYRVVSVLTVLHQDWLNGKEYKCKVSNKALPAPI EKTISKAKGQPREPQVYTLPPSRDELTKNQVSLTCLVKG FYPSDIAVEWESNGQPENNYKTTPPVLDSDGSFFLYSKL TVDKSRWQQGNVFSCSVMHEALHNHYTQKSLSLSPGK |

Example 2: Administration of the Water-Soluble DLK1-Fc Fusion Protein to Animal Models To investigate the effect of the water-soluble DLK1-Fc fusion protein prepared in Example 1 on animal models, the water-soluble DLK1 was administered to test mice as follows.

Particularly, db/db mice and C57BL/6J mice at 7 weeks were provided from Orient Co. (Seongnam, Korea). Each group was composed of 4 mice, and adapted in an animal facility maintained at 23±2° C. with 55±5% humidity and 12 hr light/12 hr dark cycle. The animals were fed with standard diet. Food intake and weights were monitored twice a week. The db/db mice were divided into two groups; DLK1-Fc fusion protein treated group (n=12) and vehicle-treated group (n=12). The DLK1-Fc fusion protein treated group was administered with 25 mg/kg of the DLK1-Fc fusion protein via intraperitoneal injection twice a week, and the vehicle-treated group was administered with the same volume of PBS instead of the DLK1-Fc fusion protein. The C57BL/6J mice were also divided into two groups. The DLK1-Fc fusion protein treated group (n=6) was administered with 15 mg/kg of DLK1-Fc fusion protein via intraperitoneal injection, while the vehicle-treated group (n=6) was administered with the same volume of PBS instead of the DLK1-Fc fusion protein. The animals were fasted for 6 hours and then sacrificed. All the experiments were approved by Institutional Animal Care and Use and Committee, Yonsei University College of Medicine (NO. 2013-0147-1).

Example 3: Separation and Culture of Primary Hepatocytes

Primary hepatocytes were obtained by the conventional two-step perfusion method (J Toxicol Environ Health 1979; 5: 551-560) with slightly modification. The liver was perfused with Hank's balanced salt solution, followed by decomposition using the buffer containing collagen type 2 (Gibco). The liver was minced on a petri dish and filtered with a 100 μm pore mesh, followed by centrifugation. After centrifugation, the precipitate was resuspended in DMEM (GE Healthcare Hyclone, Seongnam, Korea) supplemented with 2.7 mM D-glucose and 10% FBS (fetal bovine serum), followed by culture in a 37° C., 5% $CO_2$ incubator. Cell viability was measured by using trypan blue, and the cells were seeded in a collagen-coated 6-well plate ($5 \times 10^5$/well), followed by culture for 24 hours before experiment. HepG2 cells were maintained in the high glucose DMEM supplemented with 10% FBS, 100 U penicillin, and 100 μg streptomycin.

Experimental Example 1: Improvement of Hepatic Steatosis by the Water-Soluble DLK1-Fc Fusion Protein in Db/Db Mouse To investigate the effect of the water-soluble DLK1-Fc fusion protein on hepatic steatosis in db/db mouse, the water-soluble DLK1-Fc fusion protein constructed in Example 1 was administered to the animal model, followed by the measurement of hepatic triglyceride and lipid droplets.

Particularly, the water-soluble DLK1-Fc fusion protein constructed by the method of Example 1 was administered to the db/db mouse by the same manner as described in Example 2. Then, blood samples were obtained from the inferior vena cava of the mouse by using a heparin syringe. The blood samples were centrifuged at 5000×g for 15 minutes. Plasma AST (aspartate aminotransferase) and ALT (alanine aminotransferase) were measured by ELISA (Bio-Assay Systems, Hayward, Calif.). For the pharmacokinetic analysis, the blood samples were collected from the mice administered with 15 mg/kg of the water-soluble DLK1-Fc fusion protein of Example 1 via intraperitoneal injection for 72 hours. The average half life of the DLK1 was 26 hours and the plasma concentration of the DLK1-Fc fusion protein was maintained as 10 μg/ml.

As a result, as shown in FIG. 1, after treated with the DLK1-Fc fusion protein for 4 weeks, hepatic triglyceride (TG) and lipid droplets in the db/db mouse were significantly reduced (FIG. 1, views b~c). The liver weight was compared between the control and the DLK1-Fc fusion protein treated group. As a result, the glycogen content in the liver of the DLK1-Fc fusion protein treated group was increased (FIG. 1, view e), while the blood AST and ALT concentrations were significantly reduced (FIG. 1, view f).

Experimental Example 2: Inhibitory Effect of the Water-Soluble DLK1-Fc Fusion Protein on Blood Glucose and Macrophage Infiltration in Adipose Tissue of the Db/Db Mouse <2-1> Improvement of Hyperglycemia and Dyslipidemia in the Db/Db Mouse by the Administration of the DLK1-Fc Fusion Protein The following experiment was performed to investigate the effect of the water-soluble DLK1-Fc fusion protein on adipose tissue of the db/db mouse.

Particularly, the water-soluble DLK1-Fc fusion protein constructed in Example 1 was administered to the db/db mouse by the same manner as described in Example 2. The db/db mouse at 11 weeks was fasted for overnight, followed by performing oral glucose tolerance test. The db/db mouse at 11 weeks was orally administered with glucose (1 g/kg), and then blood glucose was measured by using a glucose analyzer (Accu-Check; Roche Diagnostics, Basel, Switzerland) at the time points of 30, 60, 90, 120, 180, and 240 minutes. For the insulin tolerance test (ITT), the mouse was fasted for 6 hours and then administered with human regular insulin via intraperitoneal injection. Blood samples were collected before the administration, and 30, 60, 90, and 120 minutes after the administration, followed by measuring the blood glucose level. For the measurement of fasting blood glucose, the mouse was fasted for 8 hours before the measurement. The blood glucose level was measured in tail vein by using a glucose analyzer (Accu-Check; Roche Diagnostics, Basel, Switzerland). Cholesterol and triglyceride (TG) were also measured by using an ELISA kit (Milipitas, Calif.) provided from BioVision. NEFA (non-esterified fatty acid) was also measured by ELISA (BioAssay Systems, Hayward, Calif.).

Figure 2:
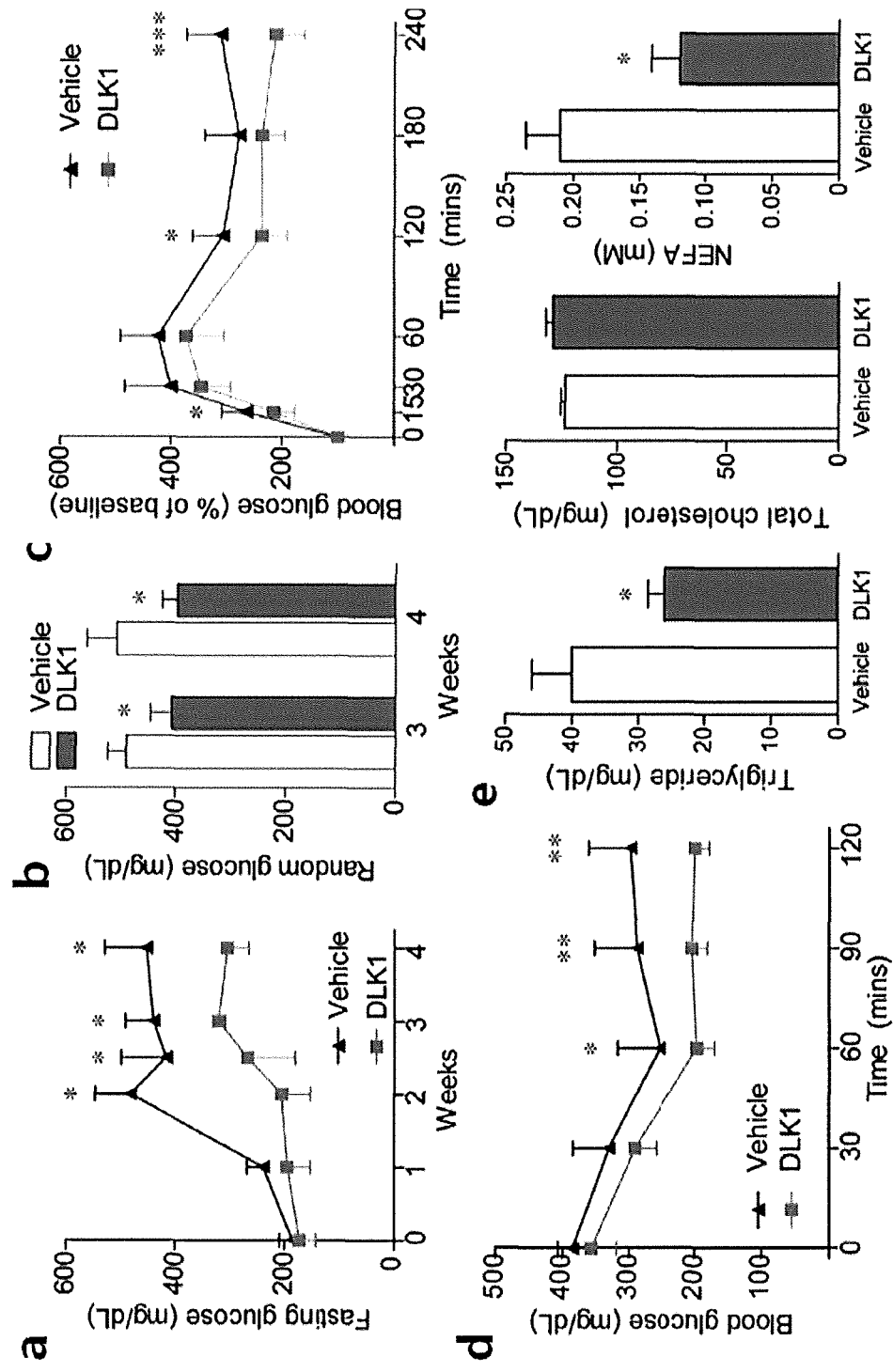
FIG. 2, inclusive of views a, b, c, d and e is a set of diagrams illustrating the improvement of high blood sugar and dyslipidemia by the DLK1-Fc fusion protein in db/db mouse FIG. 2, view a: a diagram illustrating the level of fasting blood glucose in db/db mouse FIG. 2, view b: a diagram illustrating the level of random blood glucose in db/db mouse.

As a result, as shown in FIG. 2, the fasting and random blood glucose levels were significantly reduced in the DLK1-Fc fusion protein treated mouse, compared with the control (FIG. 2, views a and b). This result suggested that the glucose and insulin resistance over the whole body was improved in the DLK1-Fc fusion protein treated group, compared with the control. Body weight, skeletal muscle, and subcutaneous and visceral fat were compared between the DLK1-Fc fusion protein treated group and the control. Both groups had the similar amount of food. As a result, blood TG and NEFA were reduced in the DLK1-Fc fusion protein treated group. In the meantime, there was no significant difference in total cholesterol between the two groups (FIG. 2, view e).

<2-2> Therapeutic Effect of the DLK1-Fc Fusion Protein on Pancreatic Islet and Adipose Tissue Inflammation in the Db/Db Mouse The following experiment was performed to investigate the therapeutic effect of the DLK1-Fc fusion protein on pancreatic islet and adipose tissue inflammation.

Particularly, the pancreas and epididymis fat body (epididymal fat pads) of the DLK1-Fc fusion protein treated db/db mouse and the control were dissected, followed by immunohistochemistry by the same manner as described in Examples 1 and 2.

First, immunohistochemistry was performed with the pancreas by using anti-insulin antibody (SC-9168, Santa Cruz). The percentage of β cell was calculated by the ratio of the total insulin-positive cell area to the total section area. The weight of β cell was calculated by multiply the β cell percentage by the total pancreas weight. The histological image was analyzed with ImageJ software program (NIH Image, Bethesda, Mass.).

To stain the epididymis fat body, the epididymis fat body separated from the db/db mouse was fixed in 10% formalin, treated with paraffin block, and then sectioned. The sections (4 μm) were stained with hematoxylin and eosin, followed by immunohistochemistry according to the conventional method for the investigation of F4/80. The antigen was recovered in citrate buffer (pH 6.0, 90° C.). The sample was treated with anti-F4/80 antibody (1:400; Abcam), and then treated again with specific biotin secondary antibody (1:100; Vector Laboratories, Burlingame, Calif.), followed by the treatment with streptavidin-peroxidase (DAKO, Kyoto, Japan). Diaminobenzidine (Vector Laboratories) was used as a chromogen and counter-staining was performed by using hematoxylin. The population of F4/80-positive cells in the section was calculated by observing at 400× and the F4/80-positive macrophage percentage was calculated by the percentage by the total cell number of each section.

Total RNA for real-time PCR was extracted according to the manufacturer's protocol by using Tirol reagent (Invitrogen). Reverse transcription was performed by using High Capacity cDNA Transcription kit (Applied Biosystems, Foster City, Calif.). Real-time PCR was performed by using ABI 7500 sequence detection system (Applied Biosystems). PCR was performed with the primers listed in Table 2 below. The quantitative analysis was performed by ΔΔcycle threshold method and StepOne software version 2.2.2.

TABLE 2

| Primer | | Sequence |
|---|---|---|
| IL-1β | Forward (SEQ ID NO: 5) | 5' CGTTCCCATTAGACA GCTGCAC-3' |
| | Reverse (SEQ ID NO: 6) | 5' TGC CAT GGT TTC TTG TGA CCC-3' |
| iNOS | Forward (SEQ ID NO: 7) | 5' CCCTTCCGAATGTTC TGGCAGCAGC-3' |
| | Reverse (SEQ ID NO: 8) | 5' GGCTGTCAGAGCCTC GTGGCTTTGG G-3' |

Figure 3:
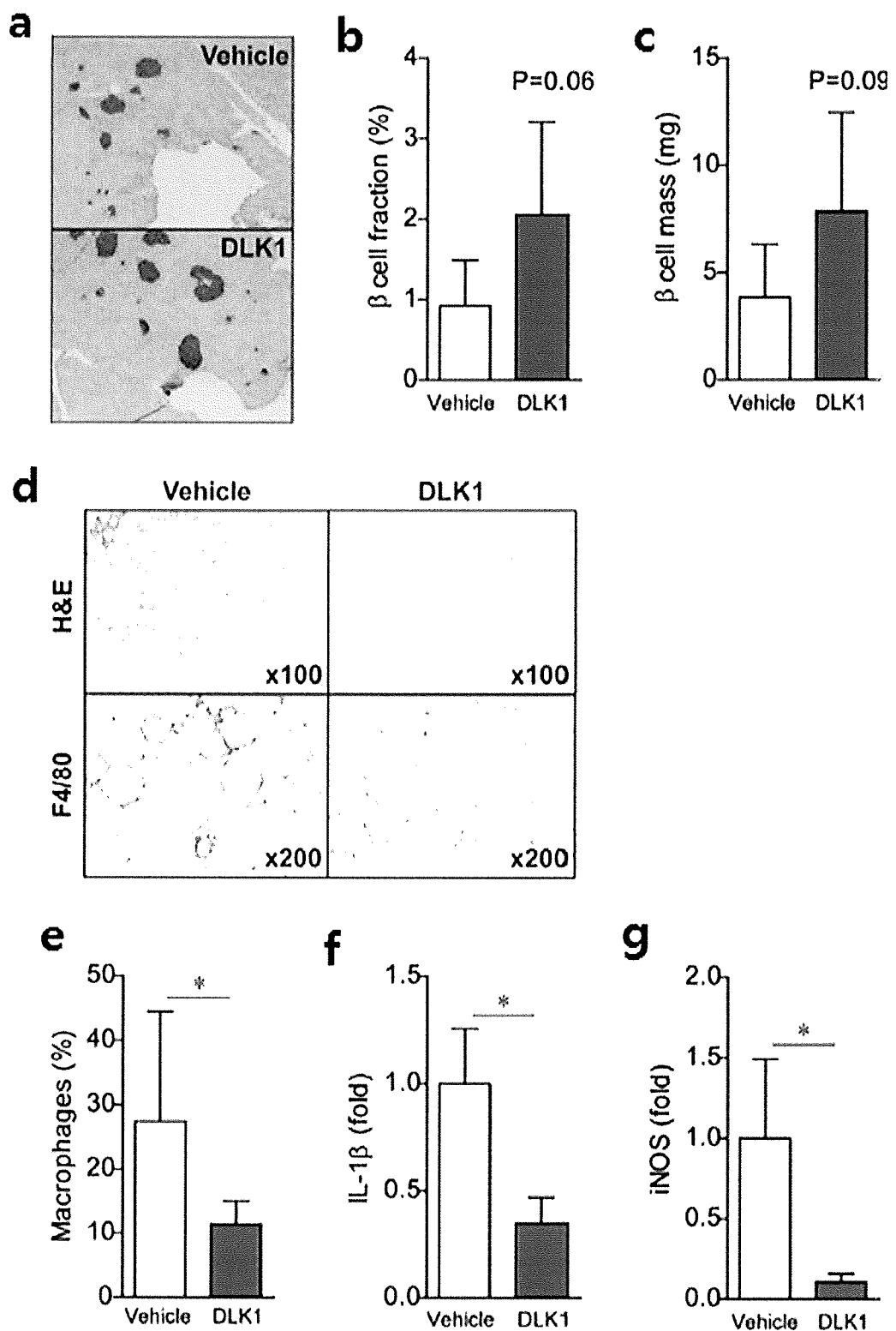
FIG. 3 inclusive of views a, b, c, d, e, f and g is a set of diagrams illustrating the therapeutic effect of the DLK1-Fc fusion protein on pancreatic islet and fat tissue inflammation in db/db mouse.

As a result, as shown in FIG. 3, the weight of the pancreatic islet of the control mouse was slightly reduced, compared with the DLK1-Fc fusion protein treated mouse (FIG. 3, views a~c). There was no big difference in the fat cell morphology between the two groups but the infiltration of F4/80-positive macrophage was significantly reduced in the DLK1-Fc fusion protein treated db/db mouse group (FIG. 3, view e). In addition, the DLK1-Fc fusion protein suppressed the mRNA expressions of inflammatory cytokines such as interleukin-1β and iNOS in the epididymis fat body (FIG. 3, views f and g).

Experimental Example 3: Inhibitory Effect of the DLK1-Fc Fusion Protein on Fat Accumulation Via AMPK Activation <3-1> Inhibitory Effect of the DLK1-Fc Fusion Protein on Fat Accumulation Via AMPK Activation In Vivo Immunoblotting and real-time PCR were performed to investigate the effect of the DLK1-Fc fusion protein prepared in Example 1 on the phosphorylations of AMPK and ACC in db/db mouse and C57BL/6J mouse.

For immunoblotting, the mouse liver treated with the DLK1-Fc fusion protein by the same manner as described in Examples 1 and 2, primary hepatocytes and HepG2 cells were lysed in RIPA buffer (Cell Signaling Technology, Danvers, Mass.), and the protein content was measured by Bradford method (Bio-Rad, 162-0115, Hercules, Calif.). Nucleic and cytoplasmic proteins were extracted from the mouse liver, primary hepatocytes, and HepG2 cells by using NE-PER kit (Pierce Biotechnology, Rockford, Ill.) according to the manufacturer's protocol. The same amount of protein (30 μg) was heat-denaturated in 4× sample buffer (2% sodium dodecyl sulfate, 62.5 mM Tris (pH 6.8), 0.01% bromophenol blue, 1.43 mM β-mercaptoethanol, and 0.1% glycerol), followed by the development on SDS-PAGE. After the development, the proteins were transferred onto nitrocellulose membranes, followed by blotting using the antibody of Table 3.

TABLE 3

| Protein | Antibody |
|---|---|
| pAMPK | cat#2535, Cell Signaling Technology |
| AMPK | cat#2603, Cell Signaling Technology |
| pACC | cat#3661, Cell Signaling Technology |
| ACC | cat#3662, Cell Signaling Technology |
| β-actin | cat#sc-47778, Santa Cruz |

For real-time PCR, total RNA was extracted according to the manufacturer's protocol by using Tirol reagent (Invitrogen). Reverse transcription was performed by using High Capacity cDNA Transcription kit (Applied Biosystems, Foster City, Calif.). Real-time PCR was performed by using ABI 7500 sequence detection system (Applied Biosystems). PCR was performed with the primers listed in Table 4 below. The quantitative analysis was performed by ΔΔcycle threshold method and StepOne software version 2.2.2.

TABLE 4

| Primer | | Sequence |
|---|---|---|
| ACADM | Forward (SEQ ID NO: 9) | 5'-TGA CGG AGC AGC CAA TGA-3' |
| | Reverse (SEQ ID NO: 10) | 5'-TCG TCA CCC TTC TTC TCT GCT T-3' |
| CPT-1a | Forward (SEQ ID NO: 11) | 5'-GGG AGG ACA GAG ACT GTA CGC TC-3' |
| | Reverse (SEQ ID NO: 12) | 5'-TGT AGG AAA CAC CAT AGC CGT CAT-3' |
| ACOX | Forward (SEQ ID NO: 13) | 5'-GGG TGG TAT GCT GTC GTA C-3' |
| | Reverse (SEQ ID NO: 14) | 5'-CAA AGA CCT TAA CGG TCA CGT AGT G-3' |

Figure 4:
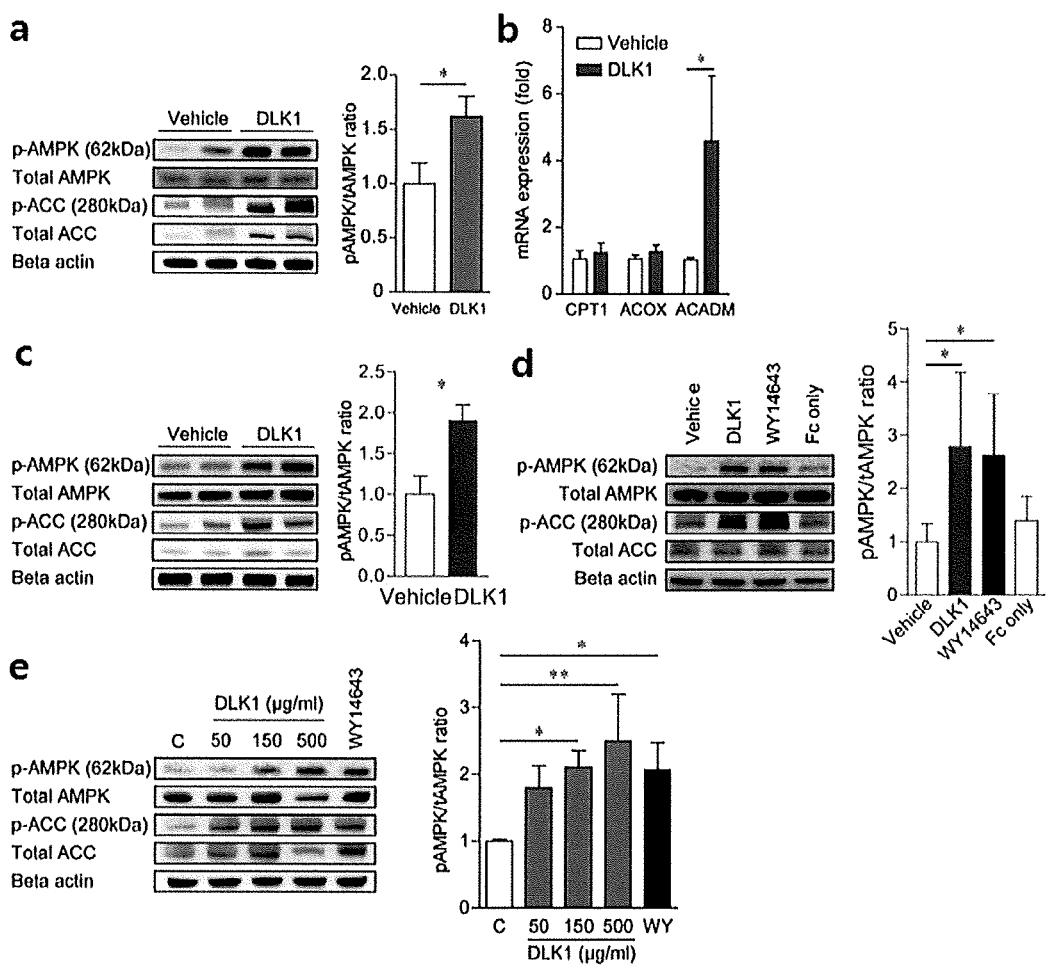
FIG. 4 inclusive of views a, b, c, d and e is a set of diagrams illustrating the DLK1-Fc fusion protein mediated AMPK activation confirmed by the investigation of the gene expression in db/db mouse, normal mouse, and hepatocyte cell line.

As a result, as shown in FIG. 4, it was confirmed that the phosphorylation of AMPK-α Thr$^{172}$ was increased in the DLK1-Fc fusion protein treated db/db mouse group (FIG. 4, view a), and the phosphorylation of acetyl-coenzyme A carboxylase (ACC), the AMPK downstream target, was also induced therein.

Among the fatty acid oxidation related genes, acyl-Coenzyme A dehydrogenase (ACADM) was significantly increased in the DLK1-Fc fusion protein treated mouse (FIG. 4, view b). The DKL1-Fc fusion protein mediated AMPK phosphorylation was re-confirmed in the DLK1-Fc fusion protein treated C57BL/6J mouse (FIG. 4, view c). In in vitro experiment using primary hepatocytes and HepG2 cells, the DLK1-Fc fusion protein mediated AMPK activation was also confirmed as equally as in vivo (FIG. 4, views d and e). DLK1 increased the phosphorylations of both AMPK and ACC dose-dependently (FIG. 4, view e). However, when the human antibody Fc alone was treated, AMPK activity was not observed (FIG., view d). The result above suggested that the DLK1-Fc fusion protein could induce fatty acid oxidation in hepatocytes via AMPK activation.

<3-2> Inhibitory Effect of the DLK1-Fc Fusion Protein on Fat Accumulation Via AMPK Activation In Vitro To investigate whether or not the DLK1-Fc fusion protein could improve fat accumulation in hepatocytes via AMPK activation in vitro, spectrophotometry using oil red O and immunoblotting were performed.

Particularly, HepG2 cells were treated with the water-soluble DLK1-Fc fusion protein constructed in Example 1 and palmitate, followed by visualization using oil red O staining and quantification. For the quantification of fat accumulation, oil red O was eluted by adding 100% isopropanol, and OD$_{520}$ was measured by spectrophotometry. Immunoblotting was performed by the same manner as described in Example <3-1>. The antibodies used herein are shown in Table 5.

TABLE 5

| Protein | Antibody |
|---|---|
| SREBP1-c | cat#PA1-46142, Thermo Fisher Scientific, Rockford, IL |
| lamin | cat#4777, Cell Signaling Technology |

Figure 5:
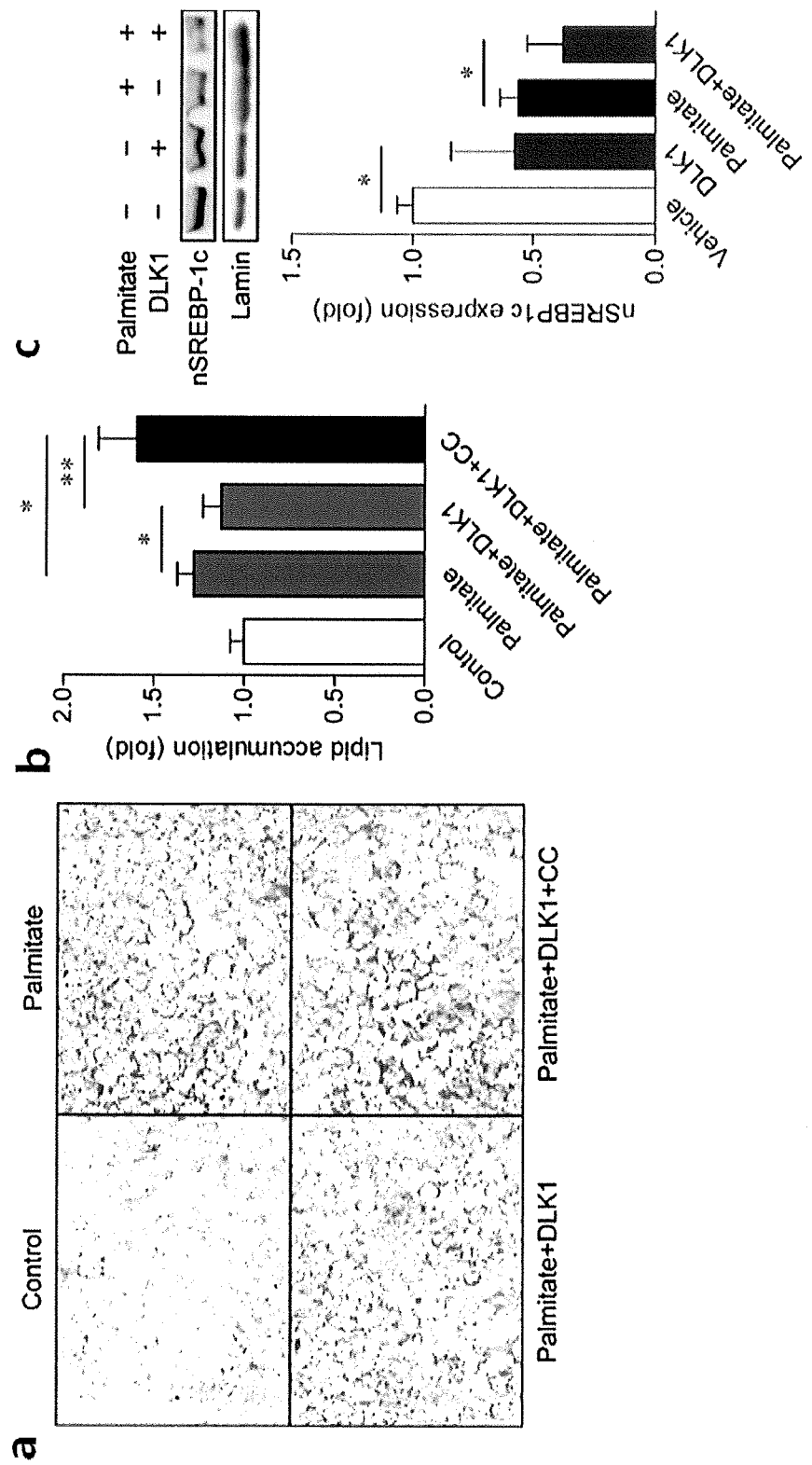
FIG. 5 inclusive of views a, b and c is a set of diagrams illustrating the inhibitory effect of DLK1 on fat accumulation in the liver by the activation of AMPK and the suppression of SREBP-1c.

As a result, as shown in Table 5, DLK1 reduced intracellular fat accumulation in the presence of palmitate, compared with the control (FIG. 5, view a and b). However, when the AMPK inhibitor compound C was pre-treated, the DLK1-Fc fusion protein did not affect fat accumulation. The DLK1-Fc fusion protein suppressed the nuclear SREBP-1C expression in HeqG2 cells in the presence of palmitate or in the control (FIG. 5, view c).

Experimental Example 4: Inhibitory Effect of the DLK1-Fc Fusion Protein on Glucogenesis in the Liver <4-1> Inhibitory Effect of the DLK1-Fc Fusion Protein on Glucogenesis in the C57BL/6J Mouse Liver The changes of glucose metabolism according to the treatment of the water-soluble DLK1-Fc fusion protein constructed in Example 1 were investigated in normal C57BL/6J mice, primary hepatocytes, and HepG2 cells.

Particularly, the experiment was performed by the same manner as described in Experimental Example <2-1>.

Figure 6:
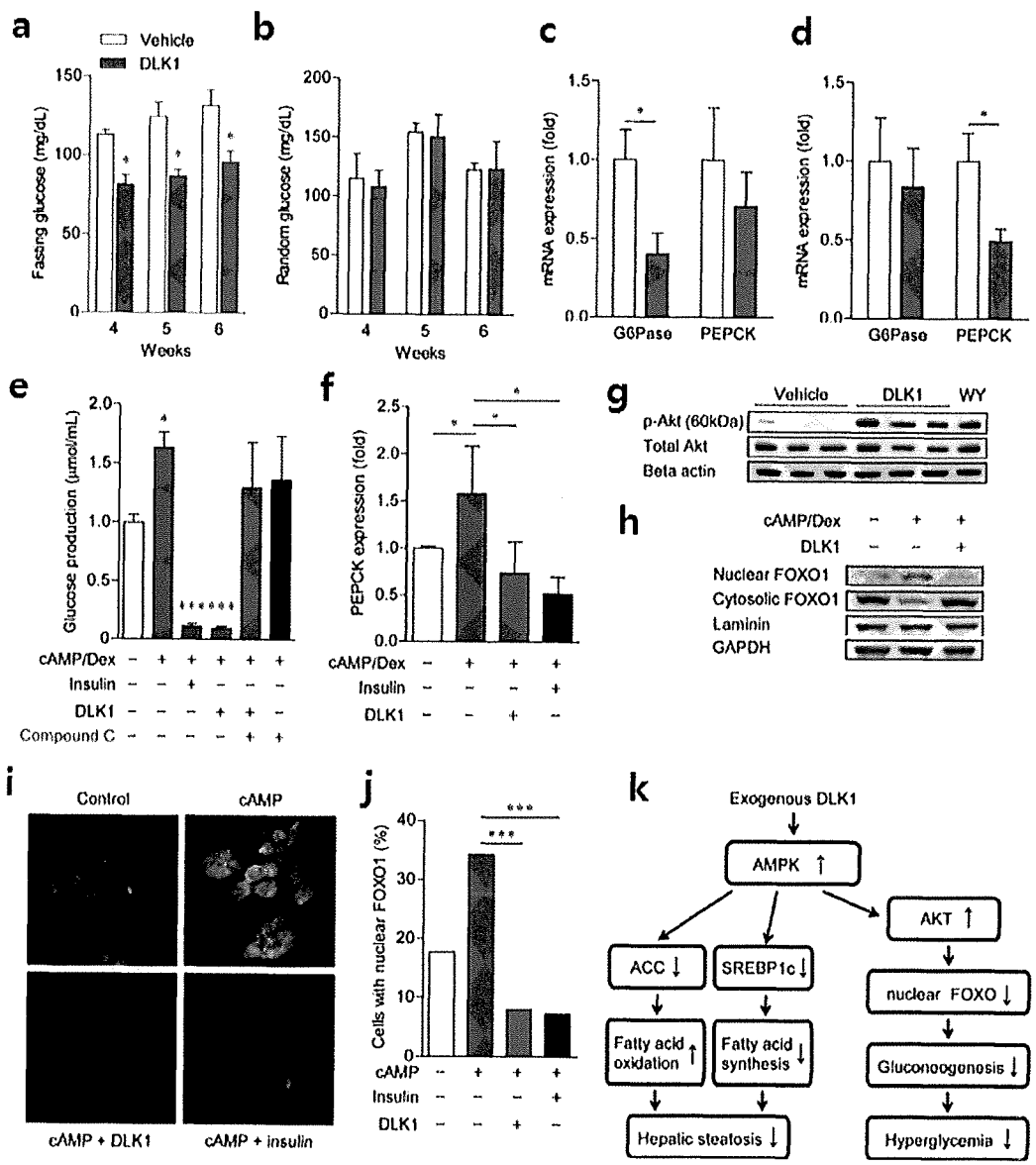
FIG. 6 inclusive of views a, b, c, d, e, f, g, h, i and k is a set of diagrams illustrating the inhibitory effect of DLK1-Fc fusion protein on glucose production in the liver through the suppression of PEPCK and G5Pase, the gluconeogenesis essential genes.
Figure 7:
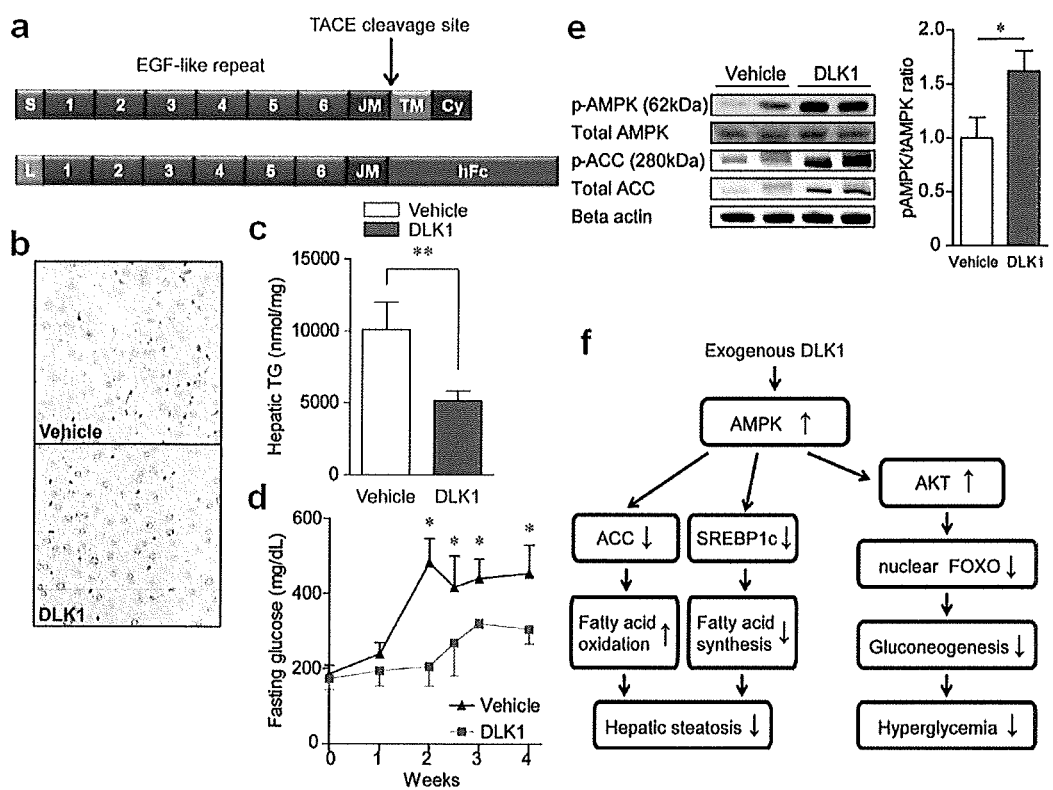
FIG. 7 inclusive of views a, b, c, d, e and f is a set of diagrams illustrating the total activity of the water-soluble DLK-1 Fc fusion protein of the present invention.

As a result, as shown in FIG. 6, the same test result was obtained from the C57BL/6J mouse group treated with the DLK1-Fc fusion protein for 6 weeks as the one obtained from the db/db mouse of FIG. 2. Compared with the control, the DLK1-Fc fusion protein treated mouse displayed a significant decrease of fasting blood glucose. However, the level of random blood glucose was not changed (FIG. 6, views a and b). Total body weight and food intake were similar between the two groups.

In addition, to explain the basic mechanism of blood sugar lowering effect of the DLK1-Fc fusion protein, the expressions of gluconeogenesis related genes such as PEPCK and G6Pase were investigated by real-time PCR by the same manner as described in Experimental Example <3-1>. The primers used herein are shown in Table 6.

TABLE 6

| Primer | | Sequence |
|---|---|---|
| PEPCK | Forward (SEQ ID NO: 15) | 5'-CTT CTC TGC CAA GGT CAT CC-3' |
| | Reverse (SEQ ID NO: 16) | 5'-GTG CCC ATC CCC AAA A-3' |
| G6Pase | Forward (SEQ ID NO: 17) | 5'-TCC TGG GAC AGA CAC ACA AG-3' |
| | Reverse (SEQ ID NO: 18) | 5'-CCA ATA GCG TAT ATT AAA GTT G-3' |
| GAPDH | Forward (SEQ ID NO: 19) | 5'-AAC TTT GGC ATT GTG GAA GG-3' |
| | Reverse (SEQ ID NO: 20) | 5'-TGT TCC TAC CCC AAT GT GT-3' |
| AMPK | Forward (SEQ ID NO: 21) | 5'-TGA CGG AGC AGC CAA TGA-3' |
| | Reverse (SEQ ID NO: 22) | 5'-TCG TCA CCC TTC TTC TCT GCT T-3' |

As a result, as shown in FIG. 6, the expressions of PEPCK and G6Pase in the DLK1-Fc fusion protein treated mouse group were approximately 50% reduced, compared with the control and the normal mouse group (FIG. 6, view c and d).

<4-2> Inhibitory Effect of the DLK1-Fc Fusion Protein on Glucogenesis in the Liver Via AMPK Activation The following experiment was performed to investigate whether or not the inhibitory effect of the DLK1-Fc fusion protein on gluconeogenesis in Experimental Example <4-1> was mediated by AMPK activation.

Particularly, HepG2 cells and primary hepatocytes were pre-treated with cAMP and Dex 6 hours before the experiment. The cells were treated with the water-soluble DLK1-Fc fusion protein constructed in Example or compound c and insulin for 6 hours and then glucose production and gene expression were measured. For the glucose production assay, primary hepatocytes and HepG2 cells were cultured in serum-free DMEM supplemented with 10 nM insulin and 25 mM glucose for 4 hours. Then, the cells were further cultured in the specific medium supplemented with 0.5 mM cAMP (adenosine 3',5'-cyclic monophosphate), 1 μm Dex (dexamethasone) (inducing gluconeogenesis), and 150 μg/ml of DLK1 or 100 mM insulin (suppressing gluconeogenesis) for 6 hours. Compound C inhibited AMPK activation. After culturing the cells in the gluconeogenesis medium (20 mM sodium lactate, 2 mM sodium pyruvate containing serum-free, glucose-free, phenol red-free DMEM) for 1~3 hours, glucose production was measured by using glucose assay kit (Abcam, Cambridge, Mass.).

The PEPCK gene expression was investigated by real-time PCR by the same manner as described in Example <4-1>. Immunoblotting was performed by using the antibodies shown in Table 7 below by the same manner as described in Experimental Example <3-1>.

TABLE 7

| Protein | Antibody |
|---------|----------|
| pAkt | cat#9271, Cell Signaling Technology |
| Akt | cat#4691, Cell Signaling Technology |
| FOXO1 | cat# sc-67140, Santa Cruz, CA |
| lamin | cat#4777, Cell Signaling Technology |
| GAPDH | cat#sc-25778, Santa Cruz |

In addition, primary hepatocytes and HepG2 cells were cultured, followed by fluorescence immunoassay to investigate the expression of FOXO1. Fluorescence immunoassay was performed according to the conventional method. The cells were plated on a chamber glass slide at the density of 1×10$^4$ cells/well, where the cells were fixed by using 4% paraformaldehyde in PBS (pH 7.4) for 5 minutes, followed by washing with PBS. The cells were blocked by using PBS containing 5% bovine serum albumin at room temperature for 2 hours. The cells were treated with the primary FOXO antibody (1:200) at 4° C. for overnight, and then treated with the secondary goat anti-rabbit IgG-FITC antibody (1:400, Invitrogen) at room temperature for 2 hours. Propidium iodide (PI, 1:1000, Invitrogen) was used for nuclear counterstaining. Images were obtained using a confocal microscope (LSM700, Carl Zeiss Inc., Oberkochen, Germany).

As a result, as shown in FIG. 6, view e, the DLK1-Fc fusion protein of the invention suppressed glucose production in both HepG2 cells and primary hepatocytes, but this inhibitory effect was suppressed by the pre-treatment of compound C. The DLK1-Fc fusion protein also suppressed the PEPCK expression induced by cAMP/Dex (FIG. 6, view f). The results above indicate that the DLK1-Fc fusion protein can inhibit glucogenesis by reducing the expression of gluconeogenesis genes such as PEPCK and G6Pase mediated by AMPK activation. According to the previous reports, the inhibition of glucogenesis in the liver was achieved by FOXO1 translocation (nucleus→4 cytoplasm) in the course of mediation by Akt phosphorylation. As shown in FIG. 6, view g, the phosphorylation of Akt was induced in HepG2 cells by the treatment of the DLK1-Fc fusion protein and the FOXO1 translocation to the nucleus induced by cAMP/Dex was inhibited. In the meantime, the treatment of DLK1 to HepG2 cells increased FOXO1 in the cytoplasm (FIG. 6, view h). The result of fluorescence immunoassay with HepG2 cells was consistent with the above (FIG. 6, views i and j). The results above indicate that the DLK1-Fc fusion protein of the invention suppresses liver gluconeogenesis through Atk and FOXO1 signal transduction pathways.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method for treating an insulin resistance-associated disease in a subject in need of treatment, said method comprising the step of administering a delta-like 1 homolog (DLK1)-Fc fusion protein constructed by conjugation of an extracellular domain of DLK1 or a fragment thereof with a human antibody Fc region, wherein the DLK1-Fc fusion protein is composed of the amino acid sequence represented by SEQ ID NO:4 and wherein the insulin resistance-associated disease is Type 2 diabetes, obesity, hypertension, hypertriglyceridemia, low high density lipoprotein (HDL) cholesterolemia, coronary artery disease, non-alcoholic fatty liver disease (NALDF) or atherosclerosis.

* * * * *

SEQUENCE LISTING

<160> NUMBER OF SEQ ID NOS: 22

<210> SEQ ID NO 1
<211> LENGTH: 383
<212> TYPE: PRT
<213> ORGANISM: Homo sapiens

<400> SEQUENCE: 1

```
Met Thr Ala Thr Glu Ala Leu Leu Arg Val Leu Leu Leu Leu Leu Ala
1               5                   10                  15

Phe Gly His Ser Thr Tyr Gly Ala Glu Cys Phe Pro Ala Cys Asn Pro
            20                  25                  30

Gln Asn Gly Phe Cys Glu Asp Asp Asn Val Cys Arg Cys Gln Pro Gly
        35                  40                  45

Trp Gln Gly Pro Leu Cys Asp Gln Cys Val Thr Ser Pro Gly Cys Leu
    50                  55                  60

His Gly Leu Cys Gly Glu Pro Gly Gln Cys Ile Cys Thr Asp Gly Trp
65                  70                  75                  80

Asp Gly Glu Leu Cys Asp Arg Asp Val Arg Ala Cys Ser Ser Ala Pro
                85                  90                  95
```

-continued

Cys Ala Asn Asn Arg Thr Cys Val Ser Leu Asp Asp Gly Leu Tyr Glu
            100                 105                 110

Cys Ser Cys Ala Pro Gly Tyr Ser Gly Lys Asp Cys Gln Lys Lys Asp
        115                 120                 125

Gly Pro Cys Val Ile Asn Gly Ser Pro Cys Gln His Gly Gly Thr Cys
    130                 135                 140

Val Asp Asp Glu Gly Arg Ala Ser His Ala Ser Cys Leu Cys Pro Pro
145                 150                 155                 160

Gly Phe Ser Gly Asn Phe Cys Glu Ile Val Ala Asn Ser Cys Thr Pro
                165                 170                 175

Asn Pro Cys Glu Asn Asp Gly Val Cys Thr Asp Ile Gly Gly Asp Phe
            180                 185                 190

Arg Cys Arg Cys Pro Ala Gly Phe Ile Asp Lys Thr Cys Ser Arg Pro
        195                 200                 205

Val Thr Asn Cys Ala Ser Ser Pro Cys Gln Asn Gly Gly Thr Cys Leu
    210                 215                 220

Gln His Thr Gln Val Ser Tyr Glu Cys Leu Cys Lys Pro Glu Phe Thr
225                 230                 235                 240

Gly Leu Thr Cys Val Lys Lys Arg Ala Leu Ser Pro Gln Gln Val Thr
                245                 250                 255

Arg Leu Pro Ser Gly Tyr Gly Leu Ala Tyr Arg Leu Thr Pro Gly Val
            260                 265                 270

His Glu Leu Pro Val Gln Gln Pro Glu His Arg Ile Leu Lys Val Ser
        275                 280                 285

Met Lys Glu Leu Asn Lys Lys Thr Pro Leu Leu Thr Glu Gly Gln Ala
290                 295                 300

Ile Cys Phe Thr Ile Leu Gly Val Leu Thr Ser Leu Val Val Leu Gly
305                 310                 315                 320

Thr Val Gly Ile Val Phe Leu Asn Lys Cys Glu Thr Trp Val Ser Asn
                325                 330                 335

Leu Arg Tyr Asn His Met Leu Arg Lys Lys Asn Leu Leu Leu Leu Gln
            340                 345                 350

Tyr Asn Ser Gly Glu Asp Leu Ala Val Asn Ile Ile Phe Pro Glu Lys
        355                 360                 365

Ile Asp Met Thr Thr Phe Ser Lys Glu Ala Gly Asp Glu Ile
    370                 375                 380

<210> SEQ ID NO 2
<211> LENGTH: 278
<212> TYPE: PRT
<213> ORGANISM: Artificial
<220> FEATURE:
<223> OTHER INFORMATION: extracellular water-soluble domain of DLK1

<400> SEQUENCE: 2

Glu Cys Phe Pro Ala Cys Asn Pro Gln Asn Gly Phe Cys Glu Asp Asp
1               5                   10                  15

Asn Val Cys Arg Cys Gln Pro Gly Trp Gln Gly Pro Leu Cys Asp Gln
            20                  25                  30

Cys Val Thr Ser Pro Gly Cys Leu His Gly Leu Cys Gly Glu Pro Gly
        35                  40                  45

Gln Cys Ile Cys Thr Asp Gly Trp Asp Gly Glu Leu Cys Asp Arg Asp
    50                  55                  60

Val Arg Ala Cys Ser Ser Ala Pro Cys Ala Asn Asn Arg Thr Cys Val
65                  70                  75                  80

-continued

Ser Leu Asp Asp Gly Leu Tyr Glu Cys Ser Cys Ala Pro Gly Tyr Ser
            85                  90                  95

Gly Lys Asp Cys Gln Lys Lys Asp Gly Pro Cys Val Ile Asn Gly Ser
        100                 105                 110

Pro Cys Gln His Gly Gly Thr Cys Val Asp Asp Glu Gly Arg Ala Ser
        115                 120                 125

His Ala Ser Cys Leu Cys Pro Pro Gly Phe Ser Gly Asn Phe Cys Glu
130                 135                 140

Ile Val Ala Asn Ser Cys Thr Pro Asn Pro Cys Glu Asn Asp Gly Val
145                 150                 155                 160

Cys Thr Asp Ile Gly Gly Asp Phe Arg Cys Arg Cys Pro Ala Gly Phe
                165                 170                 175

Ile Asp Lys Thr Cys Ser Arg Pro Val Thr Asn Cys Ala Ser Ser Pro
            180                 185                 190

Cys Gln Asn Gly Gly Thr Cys Leu Gln His Thr Gln Val Ser Tyr Glu
            195                 200                 205

Cys Leu Cys Lys Pro Glu Phe Thr Gly Leu Thr Cys Val Lys Lys Arg
210                 215                 220

Ala Leu Ser Pro Gln Gln Val Thr Arg Leu Pro Ser Gly Tyr Gly Leu
225                 230                 235                 240

Ala Tyr Arg Leu Thr Pro Gly Val His Glu Leu Pro Val Gln Gln Pro
                245                 250                 255

Glu His Arg Ile Leu Lys Val Ser Met Lys Glu Leu Asn Lys Lys Thr
            260                 265                 270

Pro Leu Leu Thr Glu Gly
        275

<210> SEQ ID NO 3
<211> LENGTH: 227
<212> TYPE: PRT
<213> ORGANISM: Artificial
<220> FEATURE:
<223> OTHER INFORMATION: human Fc fragment

<400> SEQUENCE: 3

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

-continued

```
Trp Glu Ser Asn Gly Gln Pro Glu Asn Asn Tyr Lys Thr Thr Pro Pro
            165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Lys
225

<210> SEQ ID NO 4
<211> LENGTH: 505
<212> TYPE: PRT
<213> ORGANISM: Artificial
<220> FEATURE:
<223> OTHER INFORMATION: DLK1-Fc

<400> SEQUENCE: 4

Glu Cys Phe Pro Ala Cys Asn Pro Gln Asn Gly Phe Cys Glu Asp Asp
1               5                   10                  15

Asn Val Cys Arg Cys Gln Pro Gly Trp Gln Gly Pro Leu Cys Asp Gln
            20                  25                  30

Cys Val Thr Ser Pro Gly Cys Leu His Gly Leu Cys Gly Glu Pro Gly
        35                  40                  45

Gln Cys Ile Cys Thr Asp Gly Trp Asp Gly Glu Leu Cys Asp Arg Asp
    50                  55                  60

Val Arg Ala Cys Ser Ser Ala Pro Cys Ala Asn Arg Thr Cys Val
65                  70                  75                  80

Ser Leu Asp Asp Gly Leu Tyr Glu Cys Ser Cys Ala Pro Gly Tyr Ser
                85                  90                  95

Gly Lys Asp Cys Gln Lys Lys Asp Gly Pro Cys Val Ile Asn Gly Ser
            100                 105                 110

Pro Cys Gln His Gly Gly Thr Cys Val Asp Asp Glu Gly Arg Ala Ser
        115                 120                 125

His Ala Ser Cys Leu Cys Pro Pro Gly Phe Ser Gly Asn Phe Cys Glu
    130                 135                 140

Ile Val Ala Asn Ser Cys Thr Pro Asn Pro Cys Glu Asn Asp Gly Val
145                 150                 155                 160

Cys Thr Asp Ile Gly Gly Asp Phe Arg Cys Arg Cys Pro Ala Gly Phe
                165                 170                 175

Ile Asp Lys Thr Cys Ser Arg Pro Val Thr Asn Cys Ala Ser Ser Pro
            180                 185                 190

Cys Gln Asn Gly Gly Thr Cys Leu Gln His Thr Gln Val Ser Tyr Glu
        195                 200                 205

Cys Leu Cys Lys Pro Glu Phe Thr Gly Leu Thr Cys Val Lys Lys Arg
    210                 215                 220

Ala Leu Ser Pro Gln Gln Val Thr Arg Leu Pro Ser Gly Tyr Gly Leu
225                 230                 235                 240

Ala Tyr Arg Leu Thr Pro Gly Val His Glu Leu Pro Val Gln Gln Pro
                245                 250                 255

Glu His Arg Ile Leu Lys Val Ser Met Lys Glu Leu Asn Lys Lys Thr
            260                 265                 270

Pro Leu Leu Thr Glu Gly Asp Lys Thr His Thr Cys Pro Pro Cys Pro
        275                 280                 285
```

Ala Pro Glu Leu Leu Gly Gly Pro Ser Val Phe Leu Phe Pro Pro Lys
290                 295                 300

Pro Lys Asp Thr Leu Met Ile Ser Arg Thr Pro Glu Val Thr Cys Val
305                 310                 315                 320

Val Val Asp Val Ser His Glu Asp Pro Glu Val Lys Phe Asn Trp Tyr
                325                 330                 335

Val Asp Gly Val Glu Val His Asn Ala Lys Thr Lys Pro Arg Glu Glu
            340                 345                 350

Gln Tyr Asn Ser Thr Tyr Arg Val Val Ser Val Leu Thr Val Leu His
        355                 360                 365

Gln Asp Trp Leu Asn Gly Lys Glu Tyr Lys Cys Lys Val Ser Asn Lys
370                 375                 380

Ala Leu Pro Ala Pro Ile Glu Lys Thr Ile Ser Lys Ala Lys Gly Gln
385                 390                 395                 400

Pro Arg Glu Pro Gln Val Tyr Thr Leu Pro Pro Ser Arg Asp Glu Leu
                405                 410                 415

Thr Lys Asn Gln Val Ser Leu Thr Cys Leu Val Lys Gly Phe Tyr Pro
            420                 425                 430

Ser Asp Ile Ala Val Glu Trp Glu Ser Asn Gly Gln Pro Glu Asn Asn
        435                 440                 445

Tyr Lys Thr Thr Pro Pro Val Leu Asp Ser Asp Gly Ser Phe Phe Leu
450                 455                 460

Tyr Ser Lys Leu Thr Val Asp Lys Ser Arg Trp Gln Gln Gly Asn Val
465                 470                 475                 480

Phe Ser Cys Ser Val Met His Glu Ala Leu His Asn His Tyr Thr Gln
                485                 490                 495

Lys Ser Leu Ser Leu Ser Pro Gly Lys
            500                 505

<210> SEQ ID NO 5
<211> LENGTH: 22
<212> TYPE: DNA
<213> ORGANISM: Artificial
<220> FEATURE:
<223> OTHER INFORMATION: iL 1beta forward primer

<400> SEQUENCE: 5
cgttcccatt agacagctgc ac                                          22

<210> SEQ ID NO 6
<211> LENGTH: 21
<212> TYPE: DNA
<213> ORGANISM: Artificial
<220> FEATURE:
<223> OTHER INFORMATION: iL 1beta reverse primer

<400> SEQUENCE: 6
tgccatggtt tcttgtgacc c                                           21

<210> SEQ ID NO 7
<211> LENGTH: 25
<212> TYPE: DNA
<213> ORGANISM: Artificial
<220> FEATURE:
<223> OTHER INFORMATION: iNOS forward primer

<400> SEQUENCE: 7
cccttccgaa gtttctggca gcagc                                       25

```
<210> SEQ ID NO 8
<211> LENGTH: 26
<212> TYPE: DNA
<213> ORGANISM: Artificial
<220> FEATURE:
<223> OTHER INFORMATION: iNOS reverse primer

<400> SEQUENCE: 8
ggctgtcaga gcctcgtggc tttggg                                        26

<210> SEQ ID NO 9
<211> LENGTH: 18
<212> TYPE: DNA
<213> ORGANISM: Artificial
<220> FEATURE:
<223> OTHER INFORMATION: ACADM forward primer

<400> SEQUENCE: 9
tgacggagca gccaatga                                                 18

<210> SEQ ID NO 10
<211> LENGTH: 22
<212> TYPE: DNA
<213> ORGANISM: Artificial
<220> FEATURE:
<223> OTHER INFORMATION: ACADM reverse primer

<400> SEQUENCE: 10
tcgtcaccct tcttctctgc tt                                            22

<210> SEQ ID NO 11
<211> LENGTH: 23
<212> TYPE: DNA
<213> ORGANISM: Artificial
<220> FEATURE:
<223> OTHER INFORMATION: CPT-1a forward primer

<400> SEQUENCE: 11
gggaggacag agactgtacg ctc                                           23

<210> SEQ ID NO 12
<211> LENGTH: 24
<212> TYPE: DNA
<213> ORGANISM: Artificial
<220> FEATURE:
<223> OTHER INFORMATION: CPT-1a reverse primer

<400> SEQUENCE: 12
tgtaggaaac accatagccg tcat                                          24

<210> SEQ ID NO 13
<211> LENGTH: 19
<212> TYPE: DNA
<213> ORGANISM: Artificial
<220> FEATURE:
<223> OTHER INFORMATION: ACOX forward primer

<400> SEQUENCE: 13
gggtggtatg ctgtcgtac                                                19

<210> SEQ ID NO 14
<211> LENGTH: 25
<212> TYPE: DNA
<213> ORGANISM: Artificial
<220> FEATURE:
<223> OTHER INFORMATION: ACOX reverse primer
```

<400> SEQUENCE: 14
caaagacctt aacggtcacg tagtg                                    25

<210> SEQ ID NO 15
<211> LENGTH: 20
<212> TYPE: DNA
<213> ORGANISM: Artificial
<220> FEATURE:
<223> OTHER INFORMATION: PEPCK forward primer

<400> SEQUENCE: 15
cttctctgcc aaggtcatcc                                          20

<210> SEQ ID NO 16
<211> LENGTH: 16
<212> TYPE: DNA
<213> ORGANISM: Artificial
<220> FEATURE:
<223> OTHER INFORMATION: PEPCK reverse primer

<400> SEQUENCE: 16
gtgcccatcc ccaaaa                                              16

<210> SEQ ID NO 17
<211> LENGTH: 20
<212> TYPE: DNA
<213> ORGANISM: Artificial
<220> FEATURE:
<223> OTHER INFORMATION: G6Pase forward primer

<400> SEQUENCE: 17
tcctgggaca gacacacaag                                          20

<210> SEQ ID NO 18
<211> LENGTH: 22
<212> TYPE: DNA
<213> ORGANISM: Artificial
<220> FEATURE:
<223> OTHER INFORMATION: G6Pase reverse primer

<400> SEQUENCE: 18
ccaatagcgt atattaaagt tg                                       22

<210> SEQ ID NO 19
<211> LENGTH: 20
<212> TYPE: DNA
<213> ORGANISM: Artificial
<220> FEATURE:
<223> OTHER INFORMATION: GAPDH forward primer

<400> SEQUENCE: 19
aactttggca ttgtggaagg                                          20

<210> SEQ ID NO 20
<211> LENGTH: 20
<212> TYPE: DNA
<213> ORGANISM: Artificial
<220> FEATURE:
<223> OTHER INFORMATION: GAPDH reverse primer

<400> SEQUENCE: 20
tgttcctacc cccaatgtgt                                          20

<210> SEQ ID NO 21
<211> LENGTH: 18

```
<212> TYPE: DNA
<213> ORGANISM: Artificial
<220> FEATURE:
<223> OTHER INFORMATION: AMPK forward primer

<400> SEQUENCE: 21
tgacggagca gccaatga                                                 18

<210> SEQ ID NO 22
<211> LENGTH: 22
<212> TYPE: DNA
<213> ORGANISM: Artificial
<220> FEATURE:
<223> OTHER INFORMATION: AMPK reverse primer

<400> SEQUENCE: 22
tcgtcaccct tcttctctgc tt                                            22
```